United States Patent [19]

Willard et al.

[11] Patent Number: 4,846,174
[45] Date of Patent: Jul. 11, 1989

[54] ANGIOPLASTY DILATING GUIDE WIRE

[75] Inventors: Lloyd K. Willard, Mound; Charles L. Euteneuer, St. Michael, both of Minn.

[73] Assignee: SciMed Life Systems, Inc., Minneapolis, Minn.

[21] Appl. No.: 120,366

[22] Filed: Nov. 13, 1987

Related U.S. Application Data

[63] Continuation-in-part of Ser. No. 894,658, Aug. 8, 1986, abandoned.

[51] Int. Cl.⁴ .................... A61M 29/02; A61M 29/00
[52] U.S. Cl. ..................................... 128/344; 604/95; 604/96
[58] Field of Search .............. 604/95, 104, 105, 106, 604/107, 108, 109, 101, 96; 128/343–344, 657, 772

[56] References Cited

U.S. PATENT DOCUMENTS

| | | |
|---|---|---|
| 3,896,815 | 7/1975 | Fettel et al. |
| 4,024,873 | 5/1977 | Antoshkiw et al. |
| 4,029,104 | 6/1977 | Keiber |
| 4,198,981 | 4/1980 | Sinnreich |
| 4,202,346 | 5/1980 | Granier |
| 4,276,874 | 7/1981 | Wolvek et al. |
| 4,292,974 | 10/1981 | Fogarty et al. |
| 4,307,722 | 12/1981 | Evans |
| 4,315,512 | 2/1982 | Fogarty |
| 4,327,736 | 5/1982 | Inoue |
| 4,338,942 | 7/1982 | Fogarty |
| 4,362,150 | 12/1982 | Lombardi, Jr. et al. |
| 4,403,612 | 9/1983 | Fogarty |
| 4,413,989 | 11/1983 | Schjeldahl et al. |
| 4,445,892 | 5/1984 | Hussein et al. |
| 4,448,195 | 5/1984 | LeVeen et al. |
| 4,453,545 | 6/1984 | Inoue |
| 4,467,790 | 8/1984 | Schiff |
| 4,572,186 | 2/1986 | Gould et al. |
| 4,573,470 | 3/1986 | Samson et al. |
| 4,573,966 | 5/1986 | Weikl et al. |
| 4,582,181 | 4/1986 | Samson |
| 4,619,263 | 10/1986 | Frisbie et al. |
| 4,630,609 | 12/1986 | Chin |

(List continued on next page.)

FOREIGN PATENT DOCUMENTS 348094 2/1977 Austria .
0213748 3/1987 European Pat. Off. .
WO86/06285 11/1986 PCT Int'l Appl. .

OTHER PUBLICATIONS

Article: "Transluminal Vasodilators with a Modified Dilatin Catheter", by F. Olbert & L. Hanecka (translated), Fortschritte der Medizin, Apr. 7, 1977 (West Germany).

(List continued on next page.)

Primary Examiner—C. Fred Rosenbaum
Assistant Examiner—Kathleen A. Daley
Attorney, Agent, or Firm—Merchant, Gould, Smith, Edell, Welter & Schmidt

[57] ABSTRACT

A dilating guide wire for use in percutaneous transluminal angioplasty (PTCA) has a very small outside diameter which permits it to be used with a PTCA catheter for treatment of tight stenoses in the coronary arteries that cannot be treated by conventional PTCA catheters alone. The dilating guide wire is small enough to pass through the through lumen of the PTCA catheter and extend beyond the distal tip thereof for predilating the stenosis to permit subsequent crossing and dilation by the PTCA catheter. Means may be provided for selectively imparting an axial force to the balloon of the dilating guide wire to cause axial stretching thereof, thereby reducing its profile and facilitating withdrawal of the balloon of the dilating guide wire back into the PTCA catheter. This may be accomplished through manual actuation of a control knob attached to the core, or in another embodiment, automatically through permitted limited movement of the core relative to the outer tubing of the dilating guide wire as the control manifold is moved forward or backward. According to one form of the invention, the dilating guide wire has a hollow core communicating to a small opening to the balloon area at the distal end, and venting to the atmosphere at the proximal end of the dilating guide wire, to serve as a vent for air displaced from the balloon as it is inflated with inflation fluid. The small dimensions of the vent result in self-sealing with respect to the inflation fluid.

26 Claims, 8 Drawing Sheets

U.S. PATENT DOCUMENTS

| | | |
|---|---|---|
| 4,638,805 | 1/1987 | Powell . |
| 4,646,742 | 3/1987 | Packard et al. . |
| 4,655,746 | 4/1987 | Daniels et al. . |
| 4,664,113 | 5/1987 | Frisbie et al. . |
| 4,692,200 | 9/1987 | Powell . |
| 4,715,378 | 12/1987 | Pope, Jr. et al. . |
| 4,723,936 | 2/1988 | Buchbinder et al. . |
| 4,734,093 | 3/1988 | Bonello et al. . |

OTHER PUBLICATIONS

"A New Open-Ended Guidewire/Catheter", by Thomas A. Sos, M.D., et al., *Radiology* 1985, vol. 154, pp. 817–818.

"Techniques of Renal Angioplasty", by Chas. J. Tegtmeyer, M.D., et al., *Radiology* 1986, vol. 161, pp. 577–586.

"Percutaneous Transluminal Recanalization and Dilatation of Totally Occluded Renal Arteries", by K. Sniderman, M.D., et al., *Diagnostic Radiology*, vol. 142, pp. 607–610 (Mar. 1982).

"Technique of Percutaneous Transluminal Angioplasty with the Gruntzig Balloon Catheter", by A. Gruntzig et al., *AJR*, vol. 132, 547–552 (Apr. 1979).

"Die perkutane Rekanalisation chronischer arterieller Verschlusse (Dotter-Prinzip) mit einem newuen doppellumigen Dilatationskatheter", by A. Gruntzig, *Fortschr. Rontgenstr.* 124, 1; pp. 80–86 (1976).

"Transluminal Treatment of Arteriosclerotic Obstruction", by C. T. Dotter, M.D., et al., *Circulation*, vol. XXX, pp. 654–670 (Nov. 1964).

"Occlusive Peripheral Arteriosclerosis: Treatment by Percutaneous Transluminal Recanalization-the Dotter Procedure", by M. J. Palayew, M.D., et al., *Canadian Medical Association Journal*, vol. 101, pp. 66–72 (Nov. 29, 1969).

"Transluminal Iliac Artery Dilatation", by C. T. Dotter, M.D., et al., *Journal of the American Medical Association*, vol. 230, No. 1, pp. 117–124 (Oct. 7, 1974).

"Catheter Technics in Diagnosing and Treating Femoral Artery Atherosclerosis" by C. T. Dotter, M.D., *Geriatrics* (Mar. 1984).

"Percutaneous Transluminal Coronary Angioplasty with an Over-the Wire System", by David C. Levin, M.D., et al., *Radiology* 1985, vol. 155, pp. 323–326.

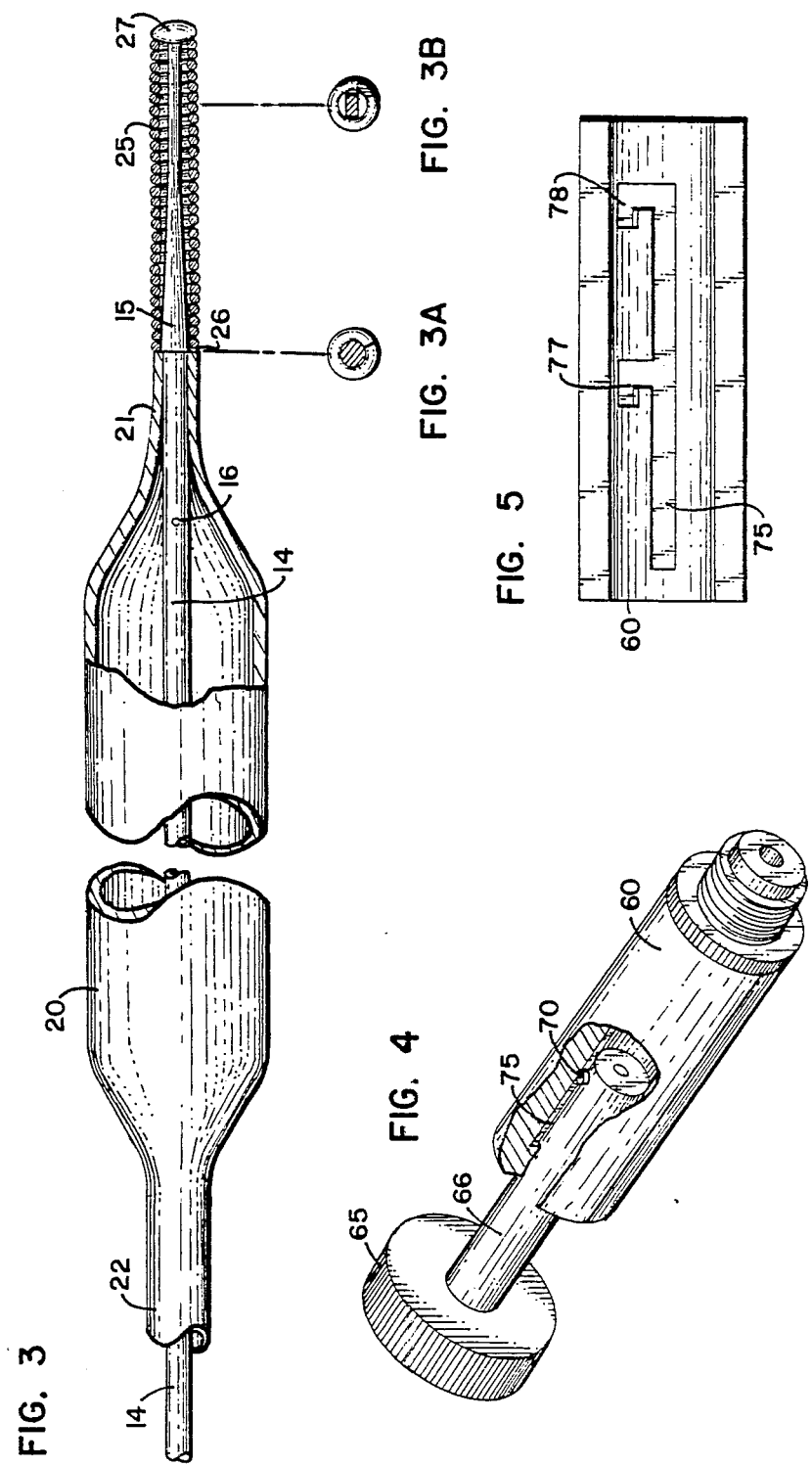

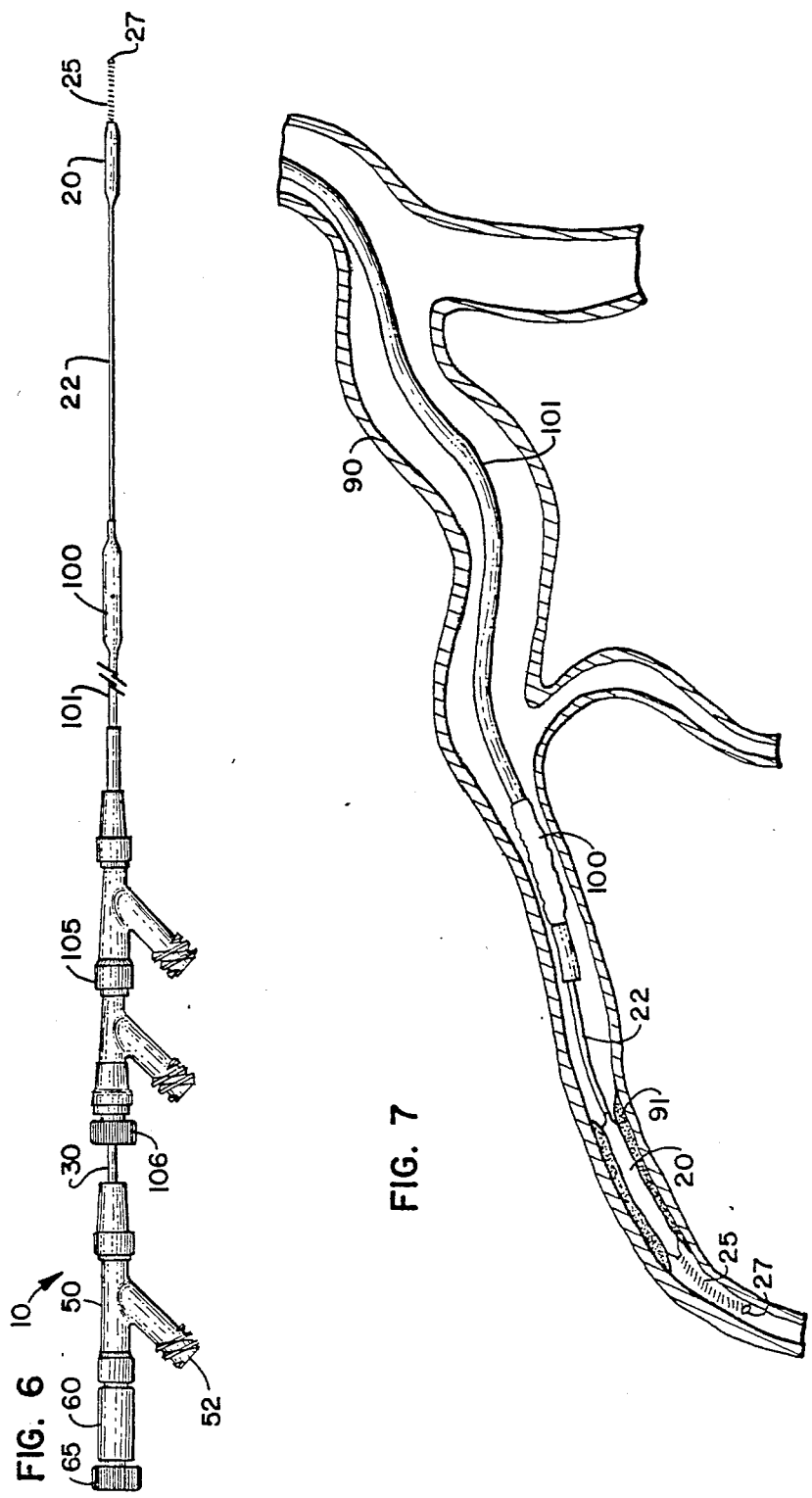

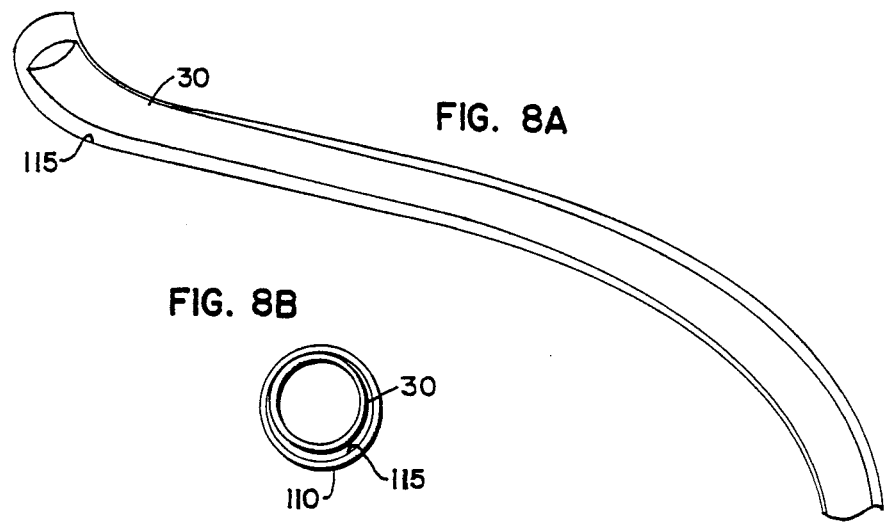
FIG. 8A
FIG. 8B
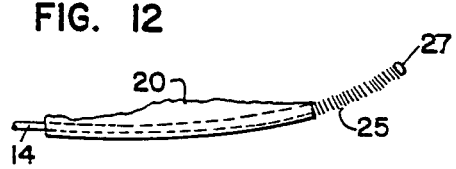
FIG. 12

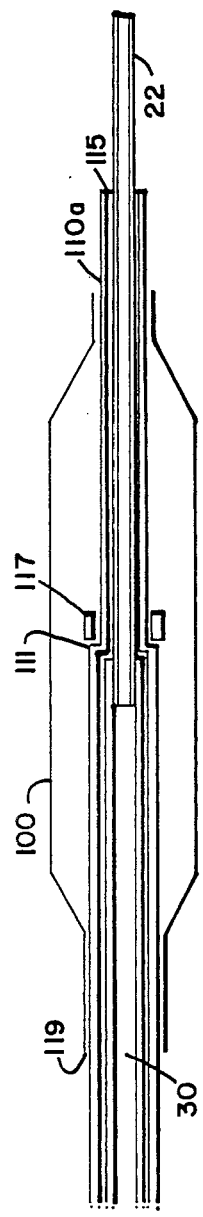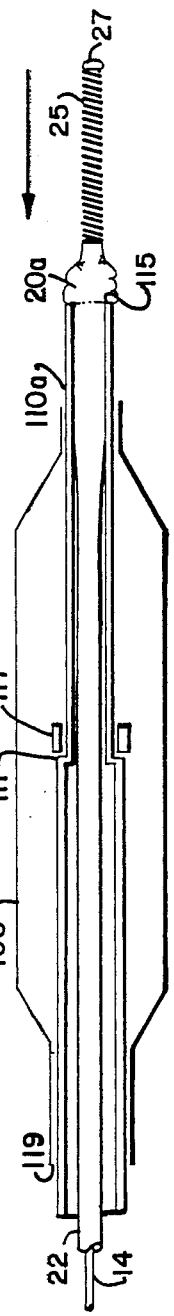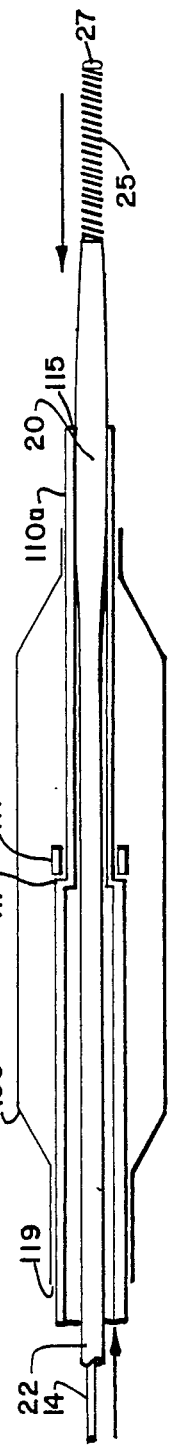

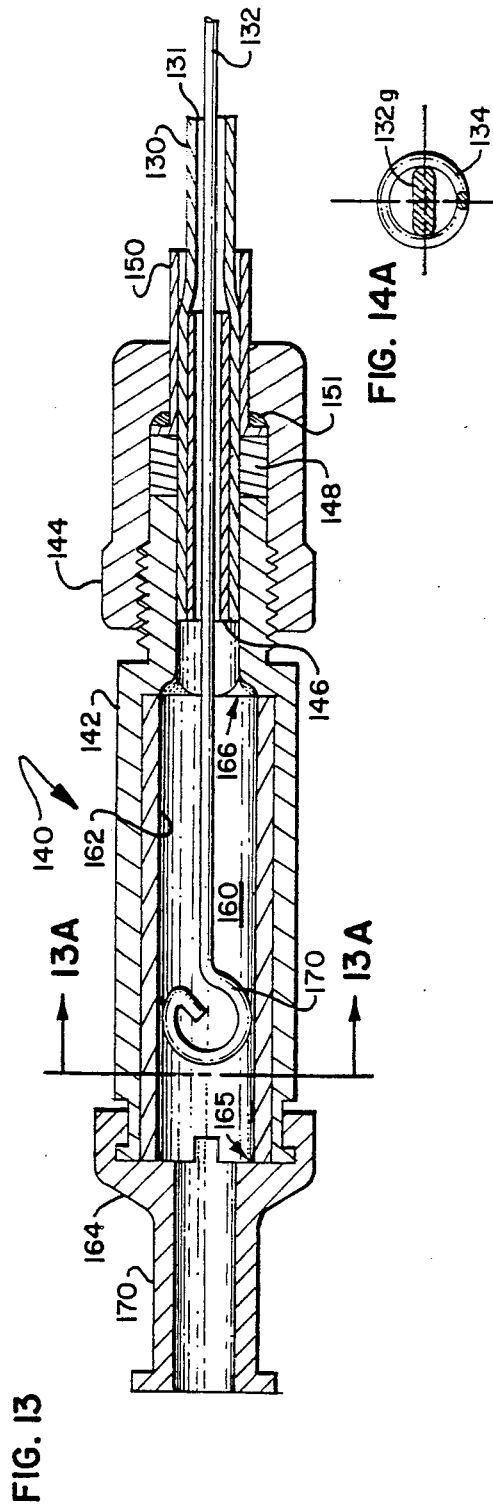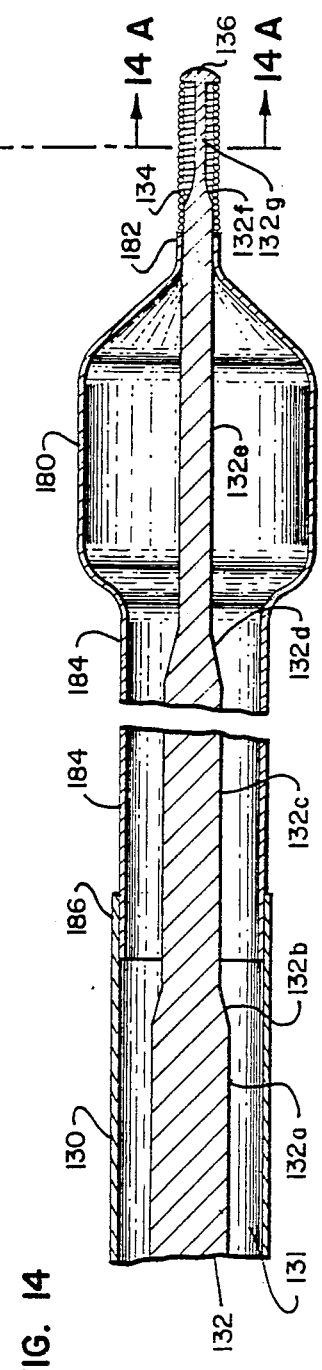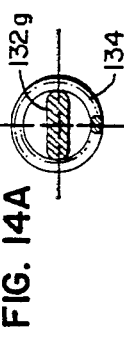

ANGIOPLASTY DILATING GUIDE WIRE

This application is a continuation-in-part of application Ser. No. 894,658, filed Aug. 8, 1986 now abandoned.

FIELD OF THE INVENTION

This invention pertains to the field of angioplasty, and particularly to the field of percutaneous transluminal angioplasty.

BACKGROUND OF THE INVENTION

Angioplasty has gained wide acceptance in recent years as an efficient and effective method for treating certain types of vascular diseases. In particular, angioplasty is widely used for opening of stenoses in the coronary arteries, although it is also used for treatment of stenoses in other parts of the vascular system. Treatment and opening of the stenosis is effected by maneuvering a catheter having an inflatable balloon area near its tip through the vascular system to position the inflatable balloon at the site of the stenosis. The balloon is then inflated to cause stretching of the artery and pressing of the lesion into the artery wall to reestablish acceptable blood flow to the artery.

Guide wires are often used for establishing the path to the stenosis so that the dilating catheter can subsequently be positioned. In percutaneous transluminal coronary angioplasty (PTCA), a steerable guide wire and PTCA catheter may be introduced into the vascular system at a site remote from the stenosis through a guiding catheter and delivered to either the left or right coronary ostia (entrance to the left and right coronary artery) by that guiding catheter. The guide wire is then maneuvered into the branch of the coronary artery for which treatment is intended. After the guide wire has been advanced past the lesion to be treated, the PTCA catheter is then positioned with its hollow central lumen at the distal tip over the end of the guide wire which is outside the body. With the guide wire held in place, the dilating catheter is then advanced over the guide wire to bring the inflatable balloon portion to the lesion. Thereafter, fluid pressure is applied through external apparatus connected to the catheter to inflate the balloon.

Various problems may be encountered in the above-described angioplasty procedure. One problem which occurs in the case of very tight stenoses with small openings is the inability to advance the dilating catheter across the stenosis after the guide wire has been successfully positioned. Since the tip of the dilating catheter has a significantly greater diameter than the guide wire, there is a practical limit to treatment of such small, tight stenoses using transluminal catheters. Efforts to reduce the diameter of the transluminal catheter are limited by the size of the guide wire. Since a clearance is required to allow the guide wire to pass with relatively minimal frictional resistance, one lumen of the transluminal design must have a diameter of at least 0.002 inch greater than the guide wire to be functional. Guide wires are available in sizes ranging from 0.012 inch to 0.018 inch in diameter. Reduced diameter guide wires have less axial strength, which may make them subject to buckling as they are being advanced, and reduced torsional stiffness, which makes them more difficult to steer and control during insertion. In addition, very small diameter guide wires might under some circumstances create a risk of injury to the blood vessels because the applied axial force is concentrated over a small tip area, which could create a risk of puncturing the artery and creating false lumens. The standard PTCA catheter, which is passed over the guide wire, is limited in size by the need to allow adequate diametral clearance between the guide wire and the inner diameter of the PTCA through channel.

Another device used in coronary angioplasty is a catheter in which a balloon is installed on a wire with a spring tip. This type of catheter offers slightly lower profiles than a transluminal design, but unlike the transluminal design cannot be used in conjunction with a conventional guide wire. Like a standard guide wire, the tips of these catheters are shaped in order to try to navigate the path from the right or left ostia to and past the vessel to be treated. The primary difficulty associated with this type of device is the inability to duplicate the performances of conventional guide wires, particularly the torsional and axial stiffness, as well as the tip flexibility and smoothness of wire transition from the core to the tip safety wire (which secures the spring tip). The second drawback of this type of device is the fact that when catheter balloon size changes are required because of the extreme difficulty of accurately estimating the artery and occlusion sizes, the entire coronary arterial path must be renegotiated with the next catheter since no guide wire is in place reserving an easily renegotiated path. Once the path has been established, it is highly desirable that the path be maintained, yet the use of single lumen systems requires loss and reestablishment of the the path.

Because of these and other problems as outlined above, there is still a need in the field of angioplasty for effective treatment of very tight stenoses with very small openings which cannot be crossed by present angioplasty catheters. Of course, it is highly desirable to be able to treat small stenoses through percutaneous coronary angioplasty techniques, since the alternative is surgical bypass grafting techniques.

SUMMARY OF THE INVENTION

The present invention provides a dilating guide wire that overcomes the problems encountered in the catheters described above. The dilating guide wire of the present invention is adapted for use in conjunction with a conventional guide wire and dilating catheter for dilatation of very tight stenoses which can then be subsequently treated with the conventional angioplasty catheter. Use of the present invention does not require loss and reestablishment of the path to the stenosis site. This is accomplished by passing the dilating guide wire through the conventional catheter while it is held in place with its tip immediately proximal the site of the stenosis.

The dilating guide wire of the present invention is configured with an extremely low profile, i.e., a very small diameter, so that it can successfully be advanced and withdrawn through the central lumen of a coaxial conventional angioplasty catheter. Special means are provided for axially extending the balloon segment of the dilation guide wire to flatten the balloon to reduce its profile. This is especially important in allowing the tip to be drawn back into the tip of the conventional dilating catheter at the end of the dilatation, and avoids bunching-up of the dilating balloon which might otherwise occur and prevent withdrawal.

According to one embodiment of the invention, this axial extending of the balloon occurs automatically as the control manifold assembly is moved inwardly or outwardly by the physician.

According to one embodiment of the invention, special means are provided in the form of a hollow core for removal of air from the dilating balloon during preparation with radiopaque liquid and which self-seals during pressurization with the liquid during balloon inflation.

According to another feature of the invention, axial stretching of the tip provides a deflection thereof which can be used for steering during positioning of the dilating tip.

According to another feature of the invention, the central core of the catheter is provided in a stepped configuration with the distal tip section which is extended into the coronary arteries from the PTCA having a smaller outer diameter and cross-sectional area than the main body of the core which is contained within the PTCA. This feature provides an extremely flexible member which is relatively non-traumatic to the coronary artery. This feature also contributes to the next features of this invention.

According to another feature of this invention, the inner diameter of the catheter inflation lumen is stepped to provide optimum hydraulic clearance which is intended for the purpose of providing an acceptable deflation time (time required to remove the entire volume of radiopaque fluid from the balloon after dilatation has been completed, thus restoring blood flow through the dilated channel) after the application of an 80% or greater vacuum. The stepped features of both the central core and the catheter tubings combined provide both the hydraulics and the profile requirement needed to provide a central balloon profile of approximately 0.020 inch for a hollow core embodiment, or 0.017 inch for a solid core embodiment of the invention.

BRIEF DESCRIPTION OF THE DRAWING

In the drawings,

FIG. 3 is a partially cut-away view at an enlarged scale of the tip portion of the dilating guide wire of FIG. 1;

FIGS. 3A and 3B are sections taken as indicated along the tip portion of FIG. 3;

FIG. 4 is a fragmentary view in perspective of a portion of the control manifold assembly of FIG. 1;

FIG. 5 is a sectional view taken along the center axis of the apparatus of FIG. 3 with the control knob removed;

FIG. 6 is a view of a dilating guide wire according to the first embodiment of the invention extending through a PTCA catheter with which it is advantageously used, including control manifolds for both the dilating guide wire and the PTCA;

FIG. 7 is a schematic representation of the use of the dilating guide wire according to the present invention in conjunction with a PTCA catheter for the treatment of a stenotic lesion in an artery;

FIGS. 8A and 8B are schematic representations in sectional view of the dilating guide wire inserted in the through lumen of the PTCA catheter;

FIG. 9 is a schematic representation at an enlarged scale of the tip area of a PTCA catheter with the dilating guide wire inserted in the through lumen thereof;

FIG. 10 is a schematic representation at an enlarged scale of the tip area of a PTCA catheter illustrating attempted withdrawal of the dilating guide wire without the use of the axial stretch feature of the invention;

FIG. 11 is a view similar to FIG. 10 but with the use of the axial stretch feature of the invention;

FIG. 12 is a view of the tip portion of the dilating guide wire illustrating the controlled deflection thereof through the use of the manually actuated axial stretch feature of one embodiment of the invention;

FIG. 13 is a cross-sectional view of a handle manifold assembly of another embodiment of the invention, which provides for automatic operation of the axial stretch feature;

FIG. 14 is a sectional view of a portion of the shaft and the tip area of another embodiment of the invention which has a solid core;

FIG. 14A is a sectional view, at an enlarged scale, taken along the line 14A—14A of FIG. 14;

DETAILED DESCRIPTION OF THE PREFERRED EMBODIMENT

Figure 1:
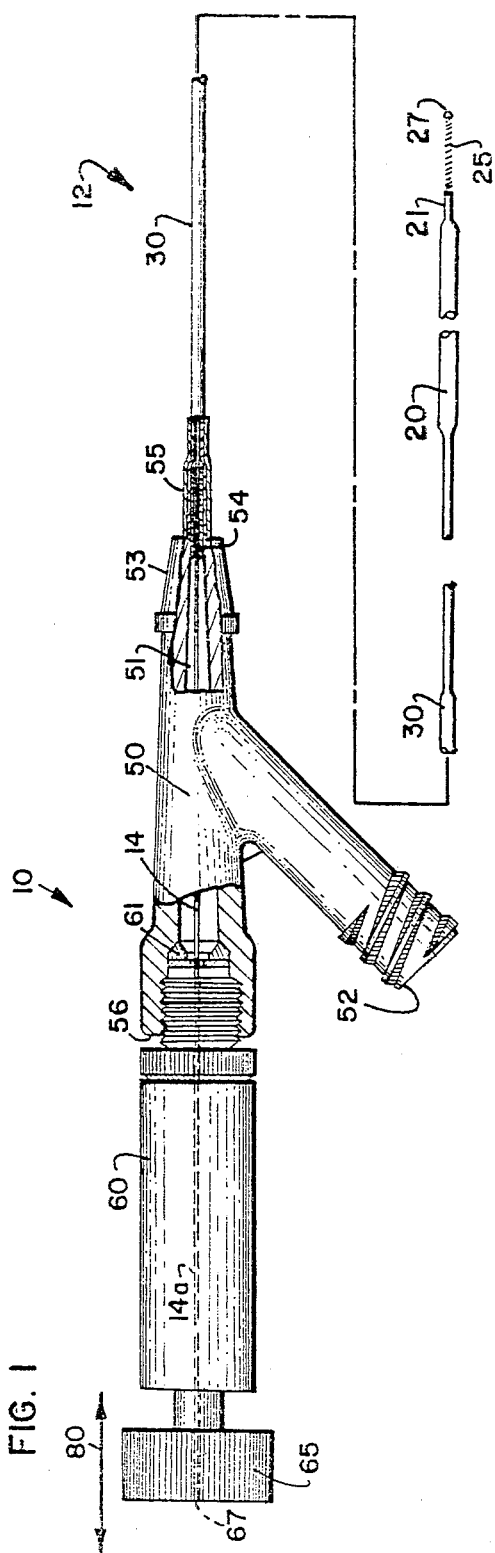
FIG. 1 is a view of a dilating guide wire according to a first embodiment of the present invention including its control manifold assembly, portions thereof broken away for purposes of illustration.

The construction of a first embodiment of the dilating guide wire is shown in FIGS. 1-5. Reference number 10 generally designates the control manifold assembly, while reference number 12 generally designates the dilating guide wire portion. Dilating guide wire portion 12 includes an inner, hollow core 14. Core 14 is made of stainless steel and extends the full length of the dilating guide wire and also substantially through the control manifold assembly 10. Core 14 is made of a suitable wall thickness and diameter for transmitting axial and torsional forces as the dilating guide wire is being advanced, while still maintaining an overall narrow diameter so that the dilating guide wire can fit through the guide wire-receiving lumen of a conventional angioplasty catheter. In the preferred embodiment the core has an outer diameter $d_3$ of 0.012 inch, which tapers or necks downwardly near the distal end to a diameter $d_1$ of 0.0075 inch throughout the region where the balloon is. Beyond the balloon, core 14 tapers again as indicated at reference number 15 to a final narrow configuration. The tapered portion 15 can be formed by a compressional step that essentially closes off the interior hollow passage of core 14 at the tip.

Tapered portion 15 is tapered from a circular section, as indicated in FIG. 3A, to a rectangular section as indicated at FIG. 3B. Although circular, square or rectangular sections can be used, the rectangular section is used in the preferred embodiment because it has the advantage of greatest flexibility for bending due to the short dimension of the rectangular section, while still maintaining sufficient cross-sectional area to preserve ultimate yield strength. The greater flexibility of the rectangular section facilitates bending of the tip by the cardiologist prior to insertion for navigation purposes, and permits the tip to orient itself to various shapes within the artery.

Balloon 20 is positioned around core 14 near the distal end of the apparatus. Balloon 20 is formed from polyolefin. The distal end 21 of the balloon 20 is bonded to core 14. The proximal end 22 extends up to outer catheter tubing 30, and is secured thereto. In the preferred embodiment, the outside diameter of the dilating guide wire at the location of distal end 21 is 0.014 inch. The diameter in the balloon area when the balloon 20 is collapsed is 0.018 to 0.020 inch.

A hole 16 is provided in the core 14 approximately adjacent the distal end of the balloon to provide an air return path as is explained in greater detail below.

Outer catheter tubing 30 is made of polyethylene as is generally known in the art and is of somewhat greater outer diameter and stiffness than the balloon. Proximal end 22 of the balloon may fit inside the inner lumen of outer catheter tubing 30 for a short distance where it is bonded thereto. The proximal end of outer catheter tubing 30 extends up to and is joined to the control manifold assembly 10.

Referring again to FIG. 3, the tip area includes a radiopaque flexible coiled spring 25 which is positioned around tapered tip 15 of the hollow core. The diameter of the coiled spring tip area is 0.012 to 0.014 inch. Coil spring 25 is brazed to core 14 at the point indicated by reference number 26 where it abuts the distal end 21 of the balloon. A smoothy radiused safety button 27 is brazed to the distal end of coil spring 25 and hollow core 14. Gold brazing is the preferred form of brazing because it does not anneal the steel around the brazed area.

The control manifold assembly includes a main housing 50 which has an interior pressure manifold or chamber 51 formed therein. Hollow core 14 extends from the dilating catheter portion 12 all the way through housing 50 and its included pressure chamber 51. A branch of housing 50 forms the inflation port 52 which communicates internally with pressure chamber 51. Inflation port 52 may have a suitable threaded fitting as shown, and is used for connection to the apparatus for applying radiopaque fluid, which is generally known in the art, for causing controlled inflation of balloon 20.

Housing 50 has a distal end 53 which receives the dilating guide wire portion 12 and which forms the end of pressure chamber 51. A short piece of relatively stiff tubing 54 is molded into distal end 53 and extends a short distance outwardly therefrom. Tubing 54 is of sufficient diameter to allow hollow core 14 to extend therethrough with sufficient clearance to provide an annular lumen for inflation of the balloon. The outer catheter tubing 30 fits over tubing 54 and is bonded thereto. A strain relief 55, for example in the form of a piece of heat-shrink tubing, fits over outer catheter tubing 30 and tube 54 to help ensure mechanical security of the assembly. The annular lumen within the dilating guide wire between outer catheter tubing 30 and hollow core 14 communicates through tube 54 to pressure chamber 51.

At the other end of housing 50 there is formed a threaded bore 56 which receives a threaded tip of a control handle housing 60. Positioned in a recess of thread bore 56 is a pressure seal 61 in the form of an O-ring. This allows hollow core 14 to pass through from housing 50 into control handle housing 60, while sealing pressure chamber 51 and preventing passage of pressurized fluid past seal 61. A control knob 65 is attached to a shaft 66 which extends into a central bore in control handle housing 60, as also seen in FIG. 4. Shaft 66 has a central bore 67 which receives hollow core 14. The proximal end of hollow core 14 is indicated by reference number 14a and is positioned within shaft 66 near the opening of central bore 67 at the end of the control knob 65. In this manner the interior core air passage of hollow core 14 is vented to the external atmosphere.

As seen in FIG. 4, shaft 66 has a tab 70 projecting therefrom. This tab works in conjunction with grooves formed in the inner wall of central bore 62 of housing 60 to limit and define the permissible motion of shaft 66. As seen in FIGS. 4 and 5, the groove includes a longitudinally extending portion indicated by reference number 75. At the forward end of groove portion 75 it connects with a hook-shaped groove portion 78. At an intermediate position groove 75 connects with another hook-shaped groove portion 77. Knob 65 may move longitudinally of the apparatus as indicated by direction arrow 80 in FIG. 1, through a limited range of motion determined by the length of groove 75.

Since the end of hollow core 14 is firmly secured in shaft 66 as by potting or the like, the above-described motion of control knob 65 causes corresponding axial movement of hollow core 14. Specifically, axial movement of knob 65 as indicated by direction arrow 80 causes axial movement of the core with respect to the outer catheter tubing 30 and causes axial stretching or relaxing of balloon 20. The system is designed so that when knob 65 is in the aft position, the balloon 20 is in the normal or unstressed condition. When knob 65 is pushed forward to bring tab 70 toward groove 78, this causes axial pushing of core 14 and stretching of balloon 20. Handle 65 can be rotated slightly to position tab 70 in the end of hook groove 78, which serves as a lock to hold the apparatus in the stretched position. The apparatus can similarly be locked with tab 70 in hook groove 77 to hold the apparatus in an intermediate position.

Axial stretching causes a reduction in profile or diameter of the balloon portion 20, as it is stretched out and thus positions itself more closely about core 14. This is explained in greater detail below with reference to FIGS. 10 and 11. When the tip area is not constrained inside a PTCA catheter, axial stretching can cause the tip portion including coil spring 25 to take a deflection toward one side, due to the nature of the axial force applied to core 14 and resisted by outer catheter tubing 30. This is indicated in FIG. 12, where the side wall of balloon 20 opposite the deflection is pulled relatively smoothly along core 14. The other side of the balloon in the direction of the deflection is also stretched out somewhat to reduce the amount of slack, but is not pulled as tightly as the other side.

Use of the present invention is illustrated with reference to FIG. 7, in which reference number 90 generally designates a portion of a patient's vascular system, specifically an artery and several branches thereof. Since the preferred embodiment of the invention is for use in treating the coronary arteries, the dilating guide wire is used in conjunction with a PTCA which is sized to cooperate with it. For that reason, the larger dilating catheter will be referred to herein as a PTCA catheter, but it will be understood that the dilating guide wire of the present invention may be used in conjunction with a dilating catheter for treatment of other arteries besides coronary arteries. The artery system includes a stenotic lesion 91 which is to be opened by angioplasty techniques. The first step is introducing a conventional guide wire in the customary manner and steering it into the appropriate branch of artery 90 to cross the lesion. (This step is not shown in FIG. 6.) Next, a PTCA catheter is advanced over the conventional guidewire. If all goes well, it is advanced across the lesion so that its balloon can be inflated to open the stenosis. However, if the stenosis is very tight, the situation is encountered where the guide wire is successfully advanced across the lesion, but the PTCA catheter cannot cross the lesion because of its too-large diameter.

When this situation is encountered, the present invention can be advantageously employed in conjunction with a PTCA catheter of the type which has a central lumen, or through lumen, through which the dilating guide wire can pass. This means that the central lumen of the angioplasty catheter in the tip area thereof must accomodate the 0.020-inch maximum outer diameter of the dilating guide wire, which is in the balloon area with the balloon collapsed, and also the slightly larger diameter of outer catheter tubing, which is not in the balloon or tip area, but which starts a distance therefrom and extends back to the manifold assembly. This is not a significant limitation on the PTCA catheter since many of them are designed to work with conventional guide wires of 0.012 to 0.018 inch. Therefore any of a number of conventional-type angioplasty catheters or PTCA catheters can be used, or a catheter especially designed to work with the dilating guide wire can be used, so long as it will receive the dilating guide wire.

In FIG. 6, the dilating guide wire is inserted in the through lumen of the PTCA catheter. The PTCA catheter includes a balloon 100, a shaft portion 101, and a manifold assembly 105, which may be of conventional design. The through lumen of the catheter is accessible through fitting 106, and the dilating guide wire, distal tip first, has been threaded and extended through the through lumen so that the tip area including balloon 20 of the dilating guide wire extends beyond the balloon 100 of the PTCA catheter. In the preferred embodiment, the dilating guide wire balloon can extend up to 5.5 inches beyond the PTCA catheter balloon.

This condition is indicated also in FIG. 9. The PTCA catheter includes an inner tubular member 110 which extends from the proximal to the distal end of the catheter. At reference number 111 in FIG. 9, approximately midway within balloon 100, tubular member 110 steps to a smaller diameter, and at this reduced diameter extends out to the distal tip as indicated by reference number 110a. This reduction in diameter helps reduce the profile of the tip portion of the catheter and increases its flexibility. Tubular member 110 has a central lumen 115 which is the through lumen of the catheter. A radiopaque marker ring 117 is attached around member 110 at the approximate midpoint of balloon 100. The proximal end of the member forming balloon 100 connects to an outer tubular member (not shown) which extends up to the manifold assembly 105. An annular inflation lumen 119 is formed between this outer tubular member and inner tubular member 110.

FIG. 9 shows the dilating guide wire inserted as far as it will go into the PTCA catheter. The step in outer diameter which occurs between the proximal end of the balloon material 22 and the distal end of outer catheter tubing 30 is accomodated by the step in inside diameter of tubular member 110 at 111. The balloon 20 of the dilating guide wire is not shown in FIG. 9, but would be off the drawing to the right thereof, approximately 5.5 inches beyond balloon 100 of the PTCA catheter.

Referring again to the situation where the PTCA catheter has been advanced over the guide wire but cannot be advanced across the lesion, the PTCA catheter is held in place, and the guide wire is withdrawn and removed from the patient. The dilating guide wire according to this invention is then introduced through the central lumen of the PTCA catheter to replace the guide wire. When the tip of the dilating guide wire emerges from the tip of the PTCA catheter it is advanced further until it crosses the lesion, which is the position indicated in FIG. 6. Balloon 20 of the dilating guide wire can then be inflated to partially compress lesion 91 and partially open the flow. The balloon and tip profile and the spring tip and core flexibility are very important in the ability to advance and cross the lesion. It is also important that the spring tip and inflated balloon are radiopaque so that the procedure can be monitored by fluoroscopy. After the balloon 20 has partly opened the flow in the artery, balloon 20 is then deflated and the dilating guide wire is advanced further down the coronary artery. The PTCA catheter is then advanced along the dilating guide wire to the lesion, which can now be successfully crossed since it has been partially dilated. The PTCA catheter can then be used in the usual manner to complete the angioplasty procedure and open the stenosis. If necessary, the conventional guide wire can be reinserted after removal of the dilating guide wire to aid in advancing the conventional catheter.

The present invention provides several useful features to aid in maneuvering the dilating guide wire to advance it across a lesion in an artery. First and foremost is the small effective diameter of the dilating guide wire, which permits it to be advanced through an angioplasty catheter in which has previously been maneuvered along a conventional guide wire to a short distance from the stenosis, typically one-half inch to one inch. Since the lesion may be around a turn in an artery or may be offset from the center of an artery, some maneuvering may still be needed. One possibility is pre-bending of the tip area as previously mentioned to give it a deflection which can then be steered by a rotation of the catheter. Another possibility is using the axial extension feature as previously discussed with reference to FIG. 12, which also will deflect the tip area. A bent or deflected tip, viewed under fluoroscopy, can be steered to cross the lesion.

The steering is advantageously accomplished by rotating the entire angioplasty catheter-dilating guide wire assembly, which can be done by manipulating the control manifold assembly 105 for the PTCA catheter. There is sufficient contact between the outer surface of tubing 30 of the dilating guide wire and the inside of the through lumen of the angioplasty catheter so as to transmit torque from the latter to the former. In the preferred embodiment, the outer diameter of outer catheter tubing 30 is 0.026 inch, and the inner diameter of tubular member 110 of the PTCA catheter is 0.030 inch. This provides sufficient clearance to allow easy insertion and withdrawal of the dilating guide wire. However, once it is in place, there will be a waving, random distribution of surface contact zones between the catheters, as suggested in FIG. 8A, as the two undergo a series of bends in various directions. This is also indicated in FIG. 8B, which shows the catheters contacting along one edge, in response to a bend. Typically, blood and/or contrast media occupy the space between the dilating guide wire and the inside wall of the through lumen of the PTCA catheter. These contact zones provide sufficient torque transmission that when the control manifold assembly 105 on the PTCA catheter is rotated, the PTCA catheter and the dilating guide wire rotate together as a unit. This takes advantage of the inherently greater torque transmission capability of the PTCA catheter, which it has by virtue of its thicker walls and larger diameter, and utilizes it for steering control of the relatively smaller and less stiff dilating guide wire. Also, the blood cells in and adjacent the zones of contact between the catheters tend to provide a high viscosity which aids in torque transmission. The net effect is that the cardiologist, viewing the procedure with the aid of fluoroscopy, has a very high degree of control over deflection of the dilating guide wire tip and steering of it to navigate the final inch or so to the lesion. The two can be advanced together as well as rotated.

Because of the small dimensions of the dilating guide wire and the demanding performance requirements it must meet, special fluid transport features and characteristics are provided. It is important that means are provided to completely purge the dilating guide wire shaft and balloon of air. This refers to the process of replacing all the air that occupied the volume of the catheter and balloon with a radiopaque contrast medium. This has been a problem with other types of catheters, and if some air remains in the balloon area it can change the radiopaque appearance of the inflated balloon, which causes difficulties for the cardiologist. The catheter must also be able to contain the pressure of the inflation applied to open the stenoses. Finally, deflation time for the balloon is very important, since the coronary artery is totally occluded during inflation of the balloon and the patient is in stress during that period. After the dilation is deemed complete by the cardiologist, it is very important that the balloon deflate rapidly, preferably in less than 20 seconds, so that blood flow is restored. The small dimensions of the balloon and core wire which are required in order to pass through the tip of a PTCA catheter can create difficulties in attaining rapid deflation rate. However, through consideration of the fluid transport parameters through the entire dilating guide wire catheter, an optimum design can be achieved which meets the low profile, strength and fluid transport requirements.

Figure 2:
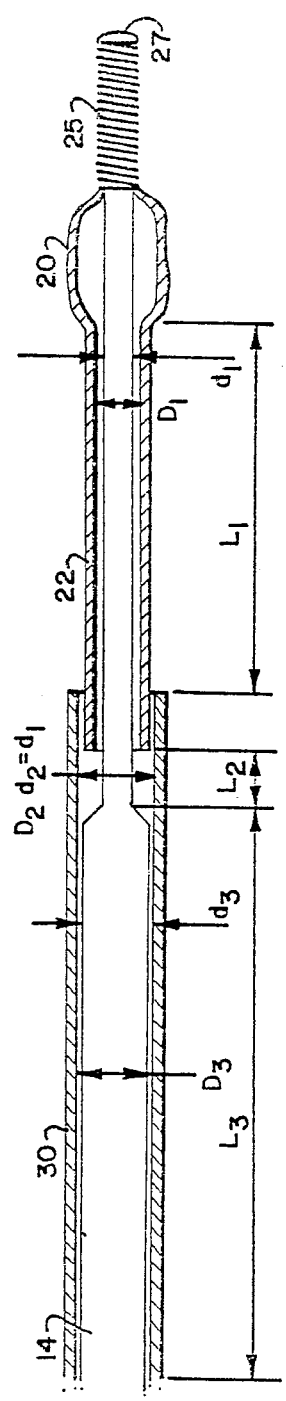
FIG. 2 is a schematic cross-sectional representation, at an enlarged scale, of a portion of the dilating guide wire of FIG. 1 illustrating certain features thereof.

FIG. 2 illustrates the important dimensions which determine the flow characteristics through the catheter. The predicted physical behavior of the flow rates can be attained using the following mathematical relation:

$Q = \Delta P / \epsilon Z$ where $\Delta P$ = differential pressure driving the fluid
$Q$ = fluid flow rate
$Z$ = fluid-surface resistive factors, and $$Z = \frac{8\eta L}{\pi B R^4 C}$$

$\eta$ = fluid kinematic viscosity
$L$ = length of fluid path
$B$ = surface friction constant
$R$ = inner radius of outer annulus channel $$C = \left[\left(1 - \left(\frac{r}{R}\right)^4\right) - \frac{\left(1 - \left(\frac{r}{R}\right)^2\right)^2}{\ln\left(\frac{R}{r}\right)}\right]$$

and $r$ = outer radius of contained member of annulus. As can be seen from the above equation, the relationship which includes a series of annuli which is the application in the fluid path of the dilating guide wire is a complex balance needed to provide the required profile that is needed to be contained within the inner lumenal path of the PTCA catheter while also providing a sufficient hydraulic channel for the balloon volume to deflate in the required 20-second maximum time frame.

In the preferred embodiment of FIGS. 1–5, the length $L_3$ of FIG. 2 is 56 inches; $L_2$ is 1.5 inches; and $L_1$ is 5.5 inches. Diameter $D_3 = D_2 = 0.020$ inch; diameter $d_3 = 0.012$ inch; $D_1 = 0.013$ inch; and, $d_1 = d_2 = 0.0075$ inch.

The purging of air from the catheter and balloon so that it can be completely filled with radiopaque contrast medium is taken care of by creating return path through the center of core 14 through which the air escapes when fluid is introduced. This path uses the central opening of hollow stainless steel drawn core 14 and aperture 16 provided therein near the distal end of the balloon. Aperture 16 is from 0.001 to 0.003 inch in diameter and communicates between the outer fluid flow channel between the balloon and tubing 22 and core 14, and the hollow central lumen of core 14. During inflation air is forced through aperture 16 and out the core as the radiopaque fluid is introduced. After the balloon has been filled and the air removed, some of the radiopaque fluid will enter aperture 16 and proceed back up the central lumen of core 14 toward the proximal end thereof. The advance of this fluid is controlled by two factors. First, the fluid column is forced through the hole 16 by pressure applied to the fluid, and fluid flow is resisted to an extent by the small diameter of the hole. Second, once the fluid has entered the central lumen of core 16, capillary action which is governed by the surface tension between the fluid and the central lumen surface characteristics and diameter will allow the fluid into the core along a certain length until a state of equilibrium is reached. At this point, more pressure would be required to begin movement of the fluid in the column than the catheter can be subject to, and therefore the fluid advances no further. This applies to both the application of positive pressure and vacuum. For this reason, the catheter is not only ventable through aperture 16 and the hollow core, but is also self-sealing. No additional seal or valve is required to prevent fluid and pressure from bleeding off through this vent passage. The flow characteristics of the radiopaque fluid in the core are dependent on optimization of the capillary action and static breakaway pressure shears.

It will be appreciated that due to the small diameter of spring 25 and the low profile of balloon 20 in its deflated state, the dilating guide wire can be advanced through a tight stenosis essentially anywhere that can be crossed by a conventional guide wire. The balloon 20 when slack tends to streamline itself and lie back along core 14 as the device is being advanced, thus providing a low profile. This low profile can be enhanced even further by pushing knob 65 forward, as discussed above, to axially stretch balloon 20 and thus further reduce its profile.

The axial stretching of the balloon is very important in withdrawing the balloon of the dilating guide wire into the PTCA catheter to remove it. After the inflation of balloon 20 has been completed, pressure is removed and the balloon deflated. At this point, if one were to attempt to withdraw the dilating guide wire back into the conventional catheter without the axial stretch feature of this invention, the undesirable effect illustrated in FIG. 10 would take place. The proximal end of the balloon 20 would withdraw into the PTCA catheter as the deflated balloon 20 would tend to streamline along hollow core 14. However, the excessive slack of the balloon, now larger due to its having been stretched in the dilating process, would tend to bunch up or accordion toward the distal end as indicated at reference number 20a, and this bunching would prevent the dilating guide wire from being fully withdrawn into and through the central lumen 115 of the PTCA catheter. To solve this problem, the axial stretch feature of the present invention is used to stretch the balloon, thus drawing it thinner and lowering its profile to permit complete withdrawal through lumen 115 as illustrated in FIG. 11. In FIG. 11, the control knob 65 of the embodiment of FIGS. 1–5 has been pushed forward and rotated to lock tab 70 in hook-shaped groove 78. This pushes the core 14 toward the distal end and stretches the balloon. This might be needed to reinsert the guide wire to advance further along the artery, and without the axial stretch feature to permit withdrawal of the dilating guide wire, it would be necessary to remove the PTCA catheter also, which would result in loss of the path.

Referring now to FIGS. 13–16, another embodiment of the invention is shown. This embodiment is generally similar to the previously described embodiment in terms of construction and use, but does differ in certain areas. In particular, the embodiment of FIGS. 13–16 provides solid core construction, even narrower profile at the tip area than the previous embodiment, and automatic operation of the axial stretch feature.

The embodiment of FIGS. 13–16, like the previous embodiment, comprises a very thin, long dilating guide wire of sufficient length from its distal tip to its proximal control manifold so as to be usable through PTCA catheters and guiding catheters in PTCA procedures. For purposes of illustration, the entire length is not shown, but FIG. 13 shows the proximal end including the control manifold assembly, and FIG. 14 shows the distal end (at an enlarged scale). The main length of the dilating guide wire is made up of outer catheter tubing 130 through which passes and core 132 which passes through it.

The proximal ends of outer catheter tubing 130 and core 132 are received in the control manifold assembly 140. The manifold assembly includes a molded plastic housing 142, which has a bore extending generally therethrough. At one end, housing 142 is threaded to receive a threaded cap portion 144. The end of outer catheter tube 130 is secured to the control manifold assembly by cap 144 as follows. A short piece of relatively stiff hypodermic tube 146 is positioned within the bore within housing 142 generally in the region of cap 144. The proximal end of outer catheter tubing 130 is flared and extends up and over hypo tube 146. A cylindrically shaped compression sleeve 148 is positioned around outer catheter tubing 130 within cap 144. A piece of tubing 150, which serves as a strain relief, fits over outer catheter tubing 130 and into the cap, where its end is flared to a flange adjacent compression sleeve 148. A manifold washer 151 is positioned adjacent this flange, and the compression sleeve 148, flange of the strain relief 150 and the manifold washer 151 are compressed between the end of housing 142 and the inside of cap 144, such that when cap 144 is threaded tightly down, the compression sleeve will push the outer catheter tubing 130 against hypo tube 146 to secure it in place to the manifold assembly. The stiffness of hypo tube 146 prevents the inflation lumen and the core 136 from being pinched off by the compression sleeve.

Figure 13A:
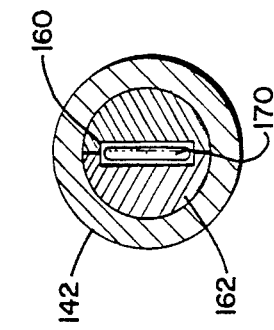
FIG. 13A is a sectional view taken along line 13A—13A of FIG. 13.

Core 132 extends through the cap area into an interior space indicated by reference number 160. In this embodiment, space 160 is in the form of an elongate slot formed by insert 162 which is positioned within housing 142. The sides of slot-like space 160 are defined by insert 162, as best seen in FIG. 13A. Insert 162 is secured against rotation within housing 142. This can be done by any suitable means, for example by gluing, or, in the preferred embodiment, by means of tabs 164 in housing 142 which mate with corresponding notches in insert 162.

Means are provided on the proximal end of core 132 to slideably position the end of core 132 within slot-like space 160. A stop member in the form of a circular or semi-circular portion 170 is bent or formed in the end of core 132. This semi-circular portion 170 is large enough to prevent the end of the core from going out the forward end of the slot area 166, or out the rearward end 165, and the circular portion 170 is planar within slot-like space 160 to prevent rotation of the core. The end of core 132 may thus freely move forwardly and backwardly over certain distance, but is constrained against rotation with respect to the control manifold assembly. It will be appreciated that instead of forming a shape 170 in the end of core 132, some other suitable stop means or members could be secured to the end of core 132 for the same purpose. In the embodiment shown, the limits of movement are defined by the point 166 where housing 142 steps to a smaller dimension, and by point 165 where pressure fitting 170 is attached. It will be appreciated, however, that other means such as inserts, projections or other equivalent means could be used to define the travel limits for the end of core 132 within space 160. The permitted travel of the end of core 132 in space 160 is for purposes of the automatic axial stretch feature of this embodiment of the invention, which is described in greater detail below.

Annular inflation lumen 131 is provided between core 132 and outer catheter tube 130, and this passes through the control manifold assembly through space 160 and pressure fitting 170. In the embodiment shown, pressure fitting 170 is a standard Luer port, which permits connection of conventional syringe or other apparatus for pressurizing/depressurizing the balloon of the catheter.

Referring now to FIG. 14, core 132 extends throughout the length of the dilating guide wire including its distal tip and balloon area. However, it undergoes several changes in profile towards the distal region. The main body of core 132, also referred to as 132a in FIG. 14, transitions at zone 132b to a lesser diameter in zone 132c. This transitions again in zone 132d to a further reduced profile zone 132e which is under the balloon area of the dilating guide wire. Zone 132e transitions at zone 132f to a further reduced profile section 132g adjacent the distal tip. In the preferred embodiment, core 132 is formed integrally from a drawn wire of biocompatible 300-series grade of stainless steel. Under the main shaft of the catheter, which is about 59 inches from the control manifold assembly to transition 132b, core 132a is approximately 0.012 inch in diameter. Zone 132c is approximately 0.0075 inch in diameter, and zone 132e, beneath the balloon, is approximately 0.006 inch. In zone 132g, the core is somewhat rectangular, as indicated in FIG. 14A, and is approximately 0.001 by 0.003 inch in cross-section. Starting from the original diameter of the wire core, zones 132c and 132e can be machined down, for example by centerless grinding or other known machining techniques, and the tip 132g can be flattened by mechanical forming techniques. In the preferred embodiment the distance from transition 132b to the distal tip of the core is approximately 10.5 inches; the distance from transition 132d to the distal tip is approximately 2.5 inches; and the distance from transition 132f to the distal tip is approximately 0.5 inch.

Platinum/iridium spring tip 134 is placed over the end of the core and brazed thereto at 135 and at the extreme tip, 136.

Outer catheter tubing 130 extends from the control manifold to a point somewhat distal of transition 132b, at which point it is bonded to the balloon segment. Tubing 130 is made of polyethylene having an outside diameter of 0.022 inch and a wall thickness of approximately 0.004 inch.

The balloon segment is formed of one piece and includes balloon portion 180, distal end portion 182, and neck portion 184. The balloon segment can be formed from a variety of polyolefin tubings and is formed via commonly known blow molding processes. Further, as it is known, irradiation cross-linking of these polymers will further link the molecular chains, thus imparting increased balloon strength and more predictable inflation diameters. Distal portion 182 is sized to fit on core zone 132e, and is bonded thereto and butted against the end 135 of the spring 134. The balloon portion 180 is approximately 20 mm in axial length, and is formed to have an inflated diameter of 1.5 mm to 2.0 mm in the preferred embodiment. It will be appreciated, however, that different inflation diameter sizes may be needed for different applications, and the principles of this invention can be used to provide similar dilating guide wires of different balloon diameters such as 2.0 mm or larger, etc. The wall thickness in the balloon portion 180 is approximately 0.0005 to 0.0001 inch. The proximal balloon portion 184 is approximately 0.0155 inch in diameter with a wall thickness of approimately 0.001 to 0.002 inch.

An advantage of the material used for balloon 180 is that it provides a certain or controlled amount of distension under pressure. Other materials are available which will go to a fixed diameter but not beyond under inflation. A problem with such materials is that they require the physician to know in advance exactly what diameter is needed for the initial dilation. Since the exact size requirement can rarely if at all be read from angiograms or fluoroscopy with that degree of certainty, a catheter exchange procedure may be required to obtain the correctly sized balloon. However, with the controlled distensible material used in the present invention, a degree of distension takes place under pressure, thus accommodating automatically for different stenoses.

The proximal end of the balloon segment is overlapped slightly by the distal end of outer catheter tubing 130, and is bonded thereto at 186. Preferably, surface preparation techniques are applied to the surfaces to be bonded, and it is preferred that this treatment be limited to the actual bonding area so that no surface roughness is imparted to the outside diameter of the catheter, which could create unwanted friction in the subsequent use of the catheter. The overall length of the balloon segment from its proximal end at bond 186 to its distal end portion 182 is approximately 7.5 inches.

One of the final steps in manufacturing is to apply a protector sleeve over the balloon area of the dilating guide wire. As seen in FIG. 16, with the balloon uninflated and folded down upon itself, a protector sleeve 190 is positioned over the balloon area. Sleeve 190 is a piece of formed Teflon tubing sized to snugly fit over the balloon area and hold it in a compactly folded form as indicated. This sleeve not only protects the tip area during shipment and subsequent handling, but it also assists in the air venting or purging process before use. Since the embodiment of FIGS. 13–16 uses a solid core rather than the vented hollow core of the previous embodiment, air purging is performed by applying a vacuum to the device. Inflation/deflation is controlled through a syringe or other pressure device (not shown) which would be attached to pressure fitting 170. Just prior to use of the dilating guide wire, the syringe is filled with the inflation fluid, which is preferably 50% contrast medium and 50% saline solution. With the balloon protector sleeve 190 still on the balloon, the syringe is attached to fitting 170. With the syringe of the nozzle pointing downward, a full vacuum is applied to the dilating guide wire for 30 seconds. The plunger is then slowly released and the syringe is removed from the control manifold assembly 140. The operator then verifies that a meniscus of contrast medium is evident in both the inflation device and the control manifold. The inflation device is then secured to the dilating guide wire control manifold. With the balloon protector 190 still in place, the dilating guide wire is tested by inflating to the recommended maximum pressure of 10 atmospheres. The catheter must exhibit no leaks and must hold pressure. The operator then applies and maintains a vacuum to the dilating guide wire, after which the balloon protector can be removed and the dilating guide wire is ready for use. By helping to hold the balloon in a compact folded configuration, the protector sleeve 190 aids in minimizing the amount of air within the balloon and inflation lumen which must be removed by the vacuum purging technique.

Figure 15:
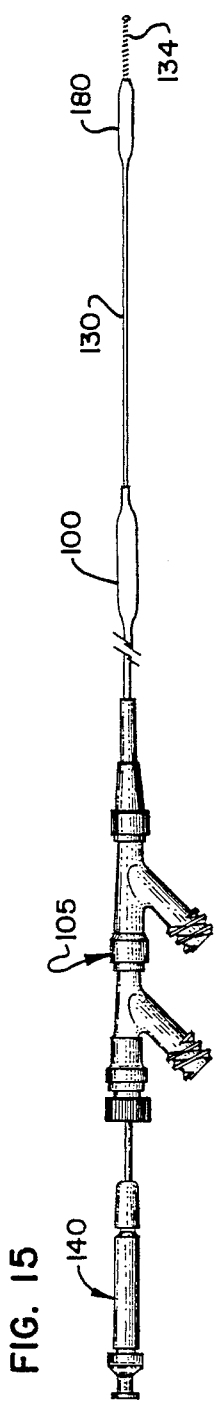
FIG. 15 is a view similar to FIG. 6 but showing the embodiment of FIG. 13 used with a conventional PTCA catheter.
Figure 16:
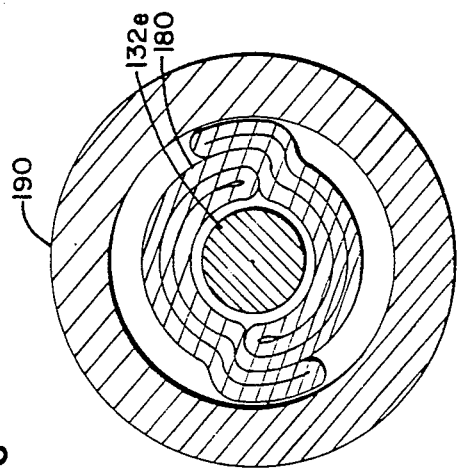
FIG. 16 is a cross-sectional view, at an enlarged scale, of a balloon portion of a dilating guide wire of the type shown in FIG. 14, with the balloon deflated and collapsed and held by a retainer.

The use of the embodiment of FIGS. 13–16 is in most respects the same as the use of the embodiment previously described. Specifically, the dilating guide wire is used by passing it through the through lumen of a conventional PTCA catheter as indicated in FIG. 15. An insertion tool (not shown), in the form of a piece of tubing with a flared end, may be used within the end of control manifold assembly 105 of the PTCA to help get the tip area of the dilating guide wire past the O-ring seals in the PTCA control manifold.

Use of the dilating guide wire for predilation of tight stenoses in the coronary arteries, to be followed by definitive dilation by the PTCA catheter, is the same as has previously been described. One difference is in the axial stretch feature. In the embodiment of FIGS. 1–5, the axial stretch is controlled manually through the operation of control 65. In the embodiment of FIGS.

13-16, the operation of the axial stretch feature is automatic. When the dilating guide wire is being advanced, through a PTCA catheter, through a coronary artery, or through a stenosis therein, the balloon is deflated and slack, and tends to streamline itself and lie back along the core 132e as the device is being advanced, thus providing a low profile. This effect is enhanced by the permitted motion of the end of core wire 132 in the control manifold assembly. As the physician advances the control manifold assembly, it will move forward until the stop member 170 engages the back limit 165 of its movement. This is due to the fact that the outer catheter tubing 130 is more flexible than core 132 and cannot transmit axial forces in the same manner that core 132 can. Thereafter, further advancing of the control manifold handle applies the axial force through core 132 to the tip of the balloon for further advancing. The effect is to permit a certain amount of slack in the balloon and outer catheter tubing to lay back or streamline itself and thereby further reduce its profile as an aid in advancement.

Upon withdrawal of the dilating guide wire, the opposite effect takes place. When control handle 140 is first pulled back, the friction and resistance along the balloon and outer catheter tubing initially causes a slight elongation thereof due to the slack and resilience of the system. This has the effect of permitting the control handle to move back until stop member 170 of the core is moved to the front of its travel in space 160 and engages engagement surface 166. Thereafter, further withdrawal movement of control handle 140 causes the force to be applied through core 132 as well as through the outer catheter tubing to withdraw the dilating guide wire. The permitted movement of the core within the dilating guide wire relative to the control handle and the outer catheter tubing results in the axial stretching in the balloon area which prevents and avoids the bunching up of the balloon, as illustrated in FIG. 10, which would otherwise occur upon attempted withdrawal back into the through lumen of the PTCA catheter. This is especially important because the balloon, after inflation, will have been stretched and will have excessive slack. However, the automatic axial stretch feature of the embodiment of FIGS. 13-16, as well as the manual axial stretch feature of the embodiment of FIGS. 1-5, both avoid this problem by providing axial stretch to the balloon area which permits withdrawal. An advantage of the automatic axial stretch feature is that it simplifies operation for the physician, since there is no need to remember to perform the specific steps of manipulating control knob 65. Also, the possibility of breaking the control mechanism by applying too much force to the knob is avoided.

The fact that the stop member 170 runs in a slot prevents relative twisting between the core and the outer catheter tubing, which, in an extreme, could cause damage or tearing. However, with the core constrained to rotate with the handle, the handle can be rotated for torque control for steering purposes.

Figure 17:
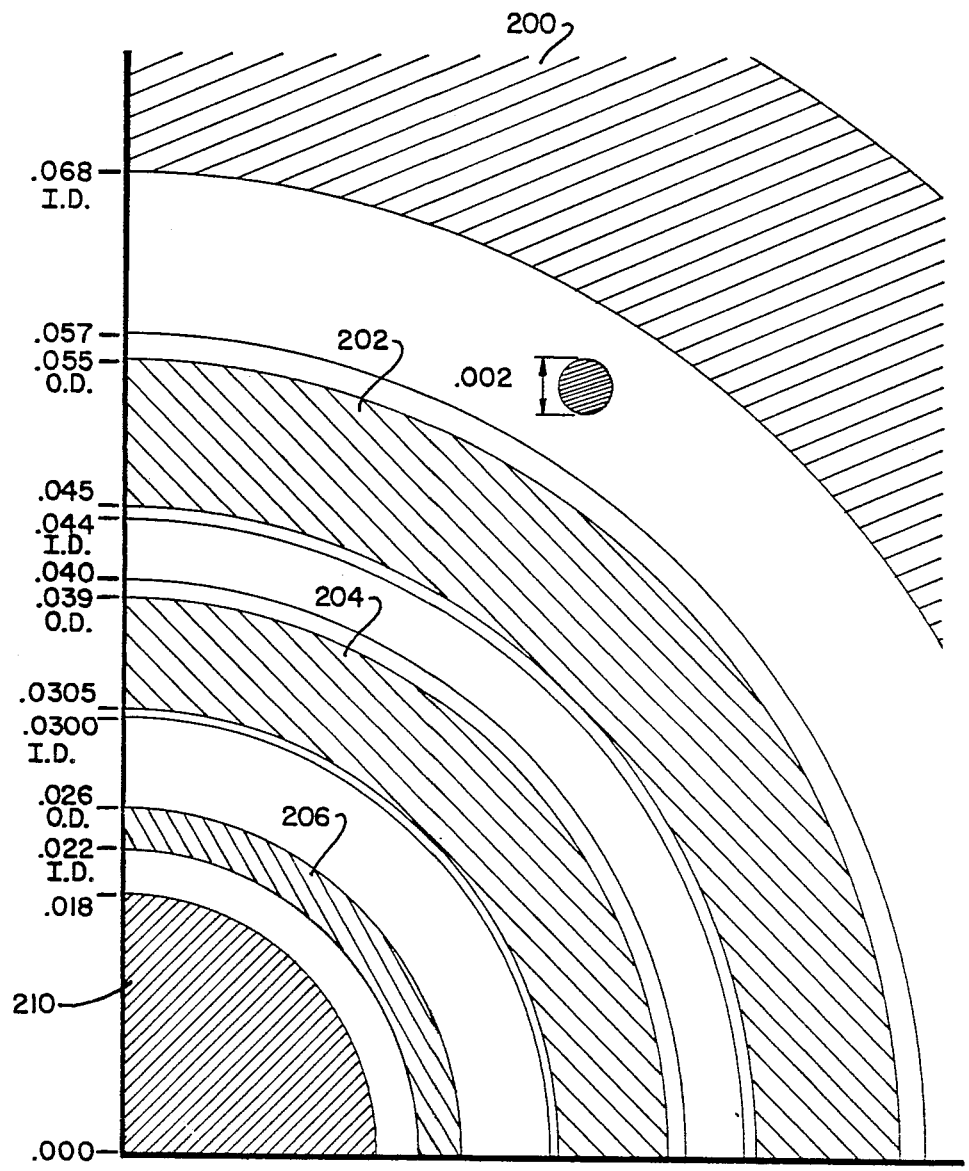
FIG. 17 is a diagram illustrating relative diameters of various components of a catheter system used in the present invention.

FIG. 17 shows relative nominal diameters of parts of the dilation system. For comparison, the 0.002-inch diameter of a human hair is also shown. Reference 200 shows the guide catheter, which typically has an inside diameter of 0.068 inch. The outer tube of the PTCA is indicated by reference 202, and has an outside diameter of 0.055 inch and an inside diameter of 0.045 inch. The inner tubular member 204 of the PTCA has an outside diameter of 0.039 inch and an inside diameter of 0.0300 inch. The extreme distal tip of the PTCA has an outside diameter of approximately 0.026 inch, and an inside diameter of 0.022 inch. This latter dimension is the narrowest part of the through lumen of the PTCA, through which the distal tip of the dilating guide wire must pass. Reference 210 designates the profile of the balloon portion of the dilating guide wire in its uninflated state. In the case of the first embodiment, this is 0.018 to 0.020 inch, while in the embodiment of FIGS. 13-16, this is 0.017 inch. The slightly smaller profile of the second embodiment provides a major advantage in terms of the clearance through the through lumen of the distal tip of the PTCA, and the freedom of friction and improved tactile feedback to the physician as the dilating guide wire is being advanced and used.

An important feature of the dilating guide wire is the rigid core extending essentially to the distal tip of the device, but transitioning to reduced profile toward the distal end. This helps provide the balance of stiffness and flexibility needed. A certain amount of stiffness is needed for pushing to advance the dilating guide wire past a stenosis, and for torqueability. The stiffness is also needed to provide tactile feedback to the physician, as a great deal of the steering and advancing involves the feel of the catheter to the physician. At the same time, the device provides the degree of flexibility and trackability needed to negotiate tortuous vasculature and stenoses without binding or causing damage. In particular, the length of the distal core segment from transition 132b to the distal tip of approximately 10.5 inches is chosen so that the thicker portion 132a of the core will remain in the guide catheter, i.e., remaining proximal to the ostia, even when the tip is at the practical extreme distal position in the heart. It is believed to be advantageous to keep the stiffer segment 132a out of the heart, where its greater stiffness could actually impede navigation. The transition thickness zone 132g is partly proximal to the ostia and partly within the heart, and provides sufficient stiffness for transmission of force to axially advance the dilating guide wire, while the lowest profile portion 132e and the tip 132g and spring 134 provide the extremely low profile and great flexibility needed to navigate to and through the stenosis.

While the use of the dilating guide wire has been explained herein in conjunction with a PTCA catheter, it may be used for other applications. For example, dilating guide wires according to the present invention are compatible with and may be used in conjunction with conventional angiographic diagnostic catheters (i.e., of the 5 French size). If in performing a conventional angiogram it appears that there is a small blockage that can be treated, a dilating guide wire according to the present invention can be introduced through the diagnostic catheter and advanced to the stenosis to do the definitive dilation thereon.

The present invention thus provides extremely low profile dilating guide wires for predilation of tight stenoses which cannot be crossed by a conventional PTCA or other angioplasty catheter. The low profile permits the device to be inserted through the PTCA in place of a guide wire, without loss of the path to the stenosis. The dilating guide wire together with a PTCA guide catheter, diagnostic catheter, or other angioplasty catheter sized to receive it form a system which can be easily steered and manipulated for predilation and subsequent dilation of the stenosis more effectively than previously feasible with other catheter types.

What is claimed is:

1. A predilatation catheter for use in angioplasty with a percutaneous transluminal coronary angioplasty (PTCA) catheter of the type having a through lumen and a distal region small enough for insertion in a coronary artery, comprising:
   an elongate flexible hollow tubular member;
   an elongate core member stiffer than said tubular member and having a diameter less than the inside diameter of said tubular member, said core member positioned inside said tubular member to define an annular inflation passage therebetween;
   means forming an inflatable balloon member adjacent the distal end of said tubular member and in fluid communication with said inflation passage with the distal end of said core member extending through the interior of said balloon;
   means for sealing the distal end of said balloon to the distal end of said core member;
   said tubular member and balloon member having an outside diameter small enough to fit within the through lumen of the PTCA catheter to permit advancing the inflatable balloon member through and beyond the distal end of the PTCA catheter;
   a control member receiving the proximal ends of said tubular member and said core member and having means for fluid communication with said annular passage for inflation and deflation of said balloon; and
   said control member including means for providing limited relative axial motion of said core member relative to said tubular member to effect axial stretching of said balloon and reduction of profile thereof whereby to facilitate withdrawing the balloon back into the distal end of the through lumen of the PTCA catheter.

2. A predilatation catheter in accordance with claim 1 wherein said tubular member is secured to said control member, and wherein said core member is received in said control member for axial movement therein between predetermined back and forward limit positions therein, whereby said core may move to its back position when said control member is pushed forward to advance the predilatation catheter, and whereby the core member may move to its forward position within said control member, thereby providing for axial stretching of the catheter and balloon as the control member is pulled to withdraw the predilatation catheter.

3. A predilatation catheter in accordance with claim 2 wherein said control member includes means for preventing substantial rotation of said core member while permitting the predetermined axial movement thereof.

4. A predilatation catheter in accordance with claim 1 wherein said control member includes a slot receiving the proximal end of said core member, wherein said core member has a stop member attached thereto within said slot so that said core may move axially of said control member within predetermined limits as the predilatation catheter is advanced or withdrawn while the core member is constrained against rotational movement relative to said control member.

5. A predilatation catheter in accordance with claim 1 wherein said core transitions to a reduced profile at the distal end of the predilatation catheter which is positioned distal to the ostia in use, and wherein the outside diameter of the distal end of the predilatation catheter with its balloon deflated is about 0.018 inch or less.

6. A predilatation catheter for use in angioplasty with a percutaneous transluminal coronary angioplasty (PTCA) catheter of the type having a through lumen and a distal region small enough for insertion in a coronary artery, comprising:
   an elongate flexible hollow tubular member;
   an elongate core member stiffer than said tubular member and having a diameter less than the inside diameter of said tubular member, said core member positioned inside said tubular member to define an annular inflation passage therebetween;
   means forming an inflatable balloon member adjacent the distal end of said tubular member and in fluid communication with said inflation passage with the distal end of said core member extending through the interior of said balloon;
   means for sealing the distal end of said balloon to the distal end of said core member;
   said tubular member and balloon member having an outside diameter small enough to fit within the through lumen of the PTCA catheter to permit advancing the inflatable balloon member through and beyond the distal end of the PTCA catheter;
   conrol means attached to the proximal end of said tubular member and having means for fluid communication with said annular passage for inflation and deflation of said balloon; and
   said control means having selectively operable means connected for applying axial force to said core member relative to said tubular member, to transmit the axial force to the distal end of said balloon to effect axial stretching and reduction of profile thereof, whereby to facilitate withdrawing the balloon back into the distal end of the through lumen of the PTCA catheter.

7. A catheter for use in angioplasty, comprising:
   an elongate flexible hollow tubular member;
   an elongate core member stiffer than said tubular member and having a diameter less than the inside diameter of said tubular member, said core member positioned inside said tubular member to define an annular inflation passage therebetween;
   means forming an inflatable balloon member adjacent the distal end of said tubular member and in fluid communication with said inflation passage, the distal end of said core member extending through the interior of said balloon;
   means for sealing the distal end of said balloon to the distal end of said core member;
   control means attached to the proximal end of said tubular member and having means for fluid communication with said annular passage for applying inflation fluid and pressure thereto to control the inflation and deflation of said balloon; and
   said core member having a fluid vent passage extending therethrough from a vent opening in the portion thereof within said balloon to an opening at or adjacent the proximal end of said core member to provide a vent path for removing air from said balloon as it is inflated with pressurized inflation fluid, the cross-sectional dimensions of said vent passage being small enough to provide self sealing of the vent passage with respect to inflation fluid entering the passage as the balloon is being inflated due to capillary action and surface tension of the fluid within the passage, whereby the inflation fluid will move along the passage only until an equilibrium is reached between the inflation pressure and the decay of pressure along the vent passage, thus effectively sealing the vent passage.

8. A catheter according to claim 7 wherein said control means includes means attached to said core member for selectively applying axial force thereto relative to said tubular member to effect axial stretching and reduction of profile of said balloon.

9. A catheter according to claim 7 wherein the outside diameter of the distal end of a catheter with the balloon deflated is about 0.02 inch or less.

10. A catheter for use in angioplasty, comprising:
an elongate flexible tubular member;
an elongate hollow metallic core, said core having a diameter less than the inside diameter of said tubular member, and positioned generally coaxially therein and having a distal end extending beyond the distal end of said tubular member;
an inflatable balloon member having one end attached adjacent the distal end of said tubular member and having its other end attached adjacent the distal end of said core with the balloon member extending around the core and in fluid communication with said annular passage;
a vent hole formed in said core in the portion thereof within said balloon to provide fluid communication between the balloon and the interior of the hollow core;
control means attached to the proximal end of said tubular member and said core and having means for introducing inflation fluid in said annular passage to inflate said balloon;
means for venting the proximal end of said hollow core to permit removal of air displaced from said balloon through said vent hole and said hollow core as the balloon is filled with inflation fluid; and
the inside dimensions of said hollow core being small enough to provide self sealing due to capillary action and surface tension with respect to inflation fluid entering therein through said vent hole as the balloon is being inflated, whereby the inflation fluid will move along the hollow core from the balloon toward the proximal end only to a point at which an equilibrium is reached between the inflation pressure and the decrease of pressure along the hollow core due to capillary action and surface tension, thus effectively forming a fluid seal.

11. A catheter according to claim 10 further including a flexible spring safety tip attached to said core at the distal end therof.

12. A catheter according to claim 10 wherein said control means includes means for attachment to said core for selectively applying axial compression force thereto relative to said tubular member, to selectively axially stretch said balloon to reduce its profile.

13. A catheter according to claim 12 wherein said means for applying axial force includes means for locking said core with respect to said tubular member with said balloon in the stretched condition.

14. Apparatus according to claim 10 wherein said core extends beyond the point of attachment of the distal end of said balloon and tapers to a smaller diameter non-hollow region, and further including a flexible safety spring disposed about and attached to the tip of said core.

15. A catheter according to claim 14 wherein said tip portion of said core tapers to a thin rectangular sectioned ribbon, to provide greater flexibility.

16. A catheter according to claim 10 wherein the outside diameter of the distal end of a catheter with the ballon deflated is about 0.02 inch or less.

17. Angioplasty apparatus for use in opening of very tight stenoses in the coronary arteries, comprising:
a PTCA catheter including an elongate tubular body adapted for introduction into a patient's vascular system, and having an inflatable balloon adjacent a distal end thereof, a through lumen, and a control handle at the proximal end thereof for controlling motion of the catheter in the vascular system and inflation of the balloon in an angioplasty procedure, the distal end of the PTCA catheter being small enough with the balloon uninflated to fit in a coronary artery;
a dilating guide wire adapted for fitting in the through lumen of said PTCA catheter, including an elongate, relatively stiff core, an elongate, relatively flexible hollow tubular member disposed generally coaxially around and along said core, an inflatable balloon at the distal end of the tubular member with its distal end sealed to the distal end of said core, a vent passage extending through said core and communicating with said balloon through a small opening in said core, said vent passage extending substantially to the proximal end but not the distal end of the core, and a control handle attached to the proximal end of said dilating guide wire to control motion thereof and inflation of said balloon with inflation fluid through an annular passage between said tubular member and said core; and
said dilating guide wire having an outside diameter small enough to permit introduction into the through lumen of said PTCA catheter through an access in the control handle thereof, and movement through said lumen to extend the balloon of said dilating guide wire beyond the balloon and distal tip of said PTCA catheter, whereby said dilating guide wire may be used to predilate a stenosis to open it sufficiently for subsequent crossing and dilation by said PTCA catheter without requiring the loss of and reestablishment of the path across the stenosis to change catheters.

18. Apparatus according to claim 17 wherein said dilating guide wire fits witin said PTCA catheter with sufficient contact for torque transmission so that the distal end of said dilating guide wire extending beyond said PTCA catheter can be rotated for steering by manual rotation of the system consisting of said PTCA catheter and said dilating guide wire.

19. Apparatus according to claim 17 wherein said dilating guide wire includes control means associated with said control handle and operatively connected for selectively imparting axial force to said core relative to the hollow tubular member to stretch the balloon of the dilating guide wire to permit withdrawing it back into the through lumen of the PTCA catheter, so that the dilating guide wire may be removed without removal of the PTCA catheter from the patient's vascular system.

20. Apparatus according to claim 17 wherein said vent passage has small enough internal dimensions to cause self sealing of inflation fluid entering therein as said balloon is inflated due to capillary action and surface tension of the inflation fluid in the vent passage.

21. Apparatus according to claim 6 wherein the outside diameter of the distal end of the predilatation catheter with its balloon deflated is about 0.02 inch or less.

22. Angioplasty apparatus for use in opening of tight stenoses in the coronary arteries, comprising:
- a PTCA catheter including an elongate tubular body adapted for introduction into a patient's vascular system, and having an inflatable balloon adjacent a distal end thereof, a through lumen, and a control means at the proximal end thereof for controlling motion of the PTCA catheter and inflation of the balloon for dilation, the distal end of the PTCA catheter when said balloon in uninflated being small enough to fit in a coronary artery;
- a dilating guide wire adapted for fitting in the through lumen of said PTCA catheter, and including an elongate core, an elongate hollow tubular member disposed generally coaxially around and along said core to define an inflation passage therebetween, an inflatable balloon adjacent the distal end of the tubular member in communication with said inflation passage, and means for sealing the distal end of said balloon so that said balloon can be inflated with inflation fluid applied thereto through said inflation passage, a vent passage in said core extending from the balloon area substantially to the proximal end of the core and communicating with said balloon through a small opening in the core to provide a path for venting displaced air as the balloon is inflated, and control means attached to the proximal end of said dilating guide wire for controlling motion thereof and inflation of said balloon with inflation fluid through said inflation passage; and
- said dilating guide wire having an outside diameter small enough, with its balloon uninflated, to permit the dilating guide wire to be placed in the through lumen of the PTCA catheter, and moved therein to extend the balloon area of said dilating guide wire beyond the distal end of said PTCA catheter, and the balloon of the dilating guide wire when inflated having a diameter greater than the uninflated diameter of the balloon of the PTCA catheter, so that the dilating guide wire may be used to predilate a stenosis to open it sufficiently for subsequent crossing and dilation by said PTCA catheter without requiring the loss of and reestablishment of the path across the stenosis to change catheters.

23. Apparatus according to claim 22 wherein said dilating guide wire fits within said PTCA catheter with sufficient contact for torque transmission so that the distal end of said dilating guide wire extending beyond said PTCA catheter can be steered by manual rotation and advancing of the system consisting of said PTCA catheter and said dilating guide wire.

24. Apparatus according to claim 22 wherein said control means of said dilating guide wire includes means operatively connected for selectively imparting axial force to said core relative to said tubular member to stretch the balloon of the dilating guide wire to permit withdrawing it back into the through lumen of the PTCA catheter.

25. Apparatus according to claim 22 wherein said vent passage within said core has small enough internal dimensions to cause self-sealing of inflation fluid entering therein as said balloon is inflated, due to capillary action and surface tension of the inflation fluid within the vent passage.

26. Apparatus according to claim 22 wherein the outside diameter of the distal end of the dilating guide wire with its balloon deflated is about 0.02 inch or less.

* * * * *

UNITED STATES PATENT AND TRADEMARK OFFICE
Certificate

Patent No. 4,846,174

Patented: July 11, 1989

On petition requesting issuance of a certificate for correction of inventorship pursuant to 35 U.S.C. 256, it has been found that the above-identified patent, through error and without any deceptive intent, improperly sets forth the inventorship. Accordingly, it is hereby certified that the correct inventorship of this patent is: Lloyd K. Willard, Charles L. Euteneuer and Jonathan Kagan.

Signed and Sealed this Eight Day of October, 1991.

C. FRED ROSENBAUM

*Supervisory Patent Examiner*
*Art Unit 336*